(12) United States Patent
Greener (10) Patent No.: US 9,801,986 B2
(45) Date of Patent: *Oct. 31, 2017

(54) VACUUM CLOSURE DEVICE

(71) Applicant: Smith & Nephew PLC, London (GB)

(72) Inventor: Bryan Greener, York (GB)

(73) Assignee: Smith & Nephew PLC, London (GB)

( * ) Notice: Subject to any disclaimer, the term of this patent is extended or adjusted under 35 U.S.C. 154(b) by 100 days.

This patent is subject to a terminal disclaimer.

(21) Appl. No.: 14/466,892

(22) Filed: Aug. 22, 2014

(65) Prior Publication Data

US 2015/0080947 A1 Mar. 19, 2015

Related U.S. Application Data

(63) Continuation of application No. 12/922,118, filed as application No. PCT/GB2009/000696 on Mar. 13, 2009, now Pat. No. 8,821,535.

(30) Foreign Application Priority Data

Mar. 13, 2008 (GB) .................................. 0804654.2

(51) Int. Cl.
*A61B 17/08* (2006.01)
*A61M 1/00* (2006.01)
(Continued)

(52) U.S. Cl.
CPC ..... *A61M 1/0088* (2013.01); *A61F 13/00068* (2013.01); *A61M 1/0001* (2013.01);
(Continued)

(58) Field of Classification Search
CPC ............. A61F 13/00068; A61M 27/00; A61M 1/0001; A61M 1/0009; A61M 1/0011; A61M 1/0023; A61M 1/0027; A61M 1/0058; A61M 1/0066; A61M 1/0088; A61M 1/009
See application file for complete search history.

(56) References Cited

U.S. PATENT DOCUMENTS 3,194,239 A 7/1965 Sullivan
3,789,851 A 2/1974 LeVeen
(Continued)

FOREIGN PATENT DOCUMENTS

CN 1438904 8/2003
CN 101112326 A 1/2008
(Continued)

OTHER PUBLICATIONS

Hougaard, et al., "The open abdomen: temporary closure with a modified negative pressure therapy technique", International Wound Journal, (2014), ISSN 1742-4801, pp. 13-16.
(Continued)

*Primary Examiner* — Robert Lynch
(74) *Attorney, Agent, or Firm* — Knobbe, Martens, Olson & Bear, LLP (57) ABSTRACT

This invention relates to the design of tissue covering elements for use in vacuum assisted tissue apposition systems, wherein the geometry of the covering elements favors the application of contractile forces over compressive or extensive forces at the tissue interface.

7 Claims, 11 Drawing Sheets

(51) Int. Cl.
*A61F 13/00* (2006.01)
*A61M 27/00* (2006.01)

(52) U.S. Cl.
CPC ............ *A61M 1/0009* (2013.01); *A61M 1/009* (2014.02); *A61M 1/0011* (2013.01); *A61M 1/0023* (2013.01); *A61M 1/0027* (2014.02); *A61M 1/0058* (2013.01); *A61M 1/0066* (2013.01); *A61M 27/00* (2013.01)

(56) References Cited

U.S. PATENT DOCUMENTS

| | | |
|---|---|---|
| 4,815,468 A | 3/1989 | Annand |
| 5,409,472 A | 4/1995 | Rawlings et al. |
| 5,415,715 A | 5/1995 | Delage et al. |
| 5,423,857 A | 6/1995 | Rosenman et al. |
| 5,512,041 A | 4/1996 | Bogart |
| 5,636,643 A | 6/1997 | Argenta et al. |
| 5,695,777 A | 12/1997 | Donovan et al. |
| 6,548,727 B1 | 4/2003 | Swenson |
| 6,566,575 B1 | 5/2003 | Stickels et al. |
| 6,685,681 B2 | 2/2004 | Lockwood et al. |
| 6,770,794 B2 | 8/2004 | Fleischmann |
| 6,787,682 B2 | 9/2004 | Gilman |
| 6,977,323 B1 | 12/2005 | Swenson |
| 7,351,250 B2 | 4/2008 | Zamierowski |
| 7,361,184 B2 | 4/2008 | Joshi |
| 7,438,705 B2 | 10/2008 | Karpowicz et al. |
| 7,494,482 B2 | 2/2009 | Orgill et al. |
| 7,615,036 B2 | 11/2009 | Joshi et al. |
| 7,625,362 B2 | 12/2009 | Boehringer et al. |
| 7,754,937 B2 | 7/2010 | Boehringer et al. |
| 7,779,625 B2 | 8/2010 | Joshi et al. |
| 7,815,616 B2 | 10/2010 | Boehringer et al. |
| 7,857,806 B2 | 12/2010 | Karpowicz et al. |
| 7,884,258 B2 | 2/2011 | Boehringer et al. |
| 7,896,856 B2 | 3/2011 | Petrosenko et al. |
| 7,909,805 B2 | 3/2011 | Weston |
| 7,931,774 B2 | 4/2011 | Hall et al. |
| 7,942,866 B2 | 5/2011 | Radl et al. |
| 7,951,124 B2 | 5/2011 | Boehringer et al. |
| 7,976,519 B2 | 7/2011 | Bubb et al. |
| 7,976,524 B2 | 7/2011 | Kudo et al. |
| 7,981,098 B2 | 7/2011 | Boehringer et al. |
| 8,030,534 B2 | 10/2011 | Radl et al. |
| 8,062,331 B2 | 11/2011 | Zamierowski |
| 8,070,773 B2 | 12/2011 | Zamierowski |
| 8,114,126 B2 | 2/2012 | Heaton et al. |
| 8,123,781 B2 | 2/2012 | Zamierowski |
| 8,133,211 B2 | 3/2012 | Cavanaugh, II et al. |
| 8,142,419 B2 | 3/2012 | Heaton et al. |
| 8,147,468 B2 | 4/2012 | Barta et al. |
| 8,172,816 B2 | 5/2012 | Kazala, Jr. et al. |
| 8,187,237 B2 | 5/2012 | Seegert |
| 8,188,331 B2 | 5/2012 | Barta et al. |
| 8,197,467 B2 | 6/2012 | Heaton et al. |
| 8,202,261 B2 | 6/2012 | Kazala, Jr. et al. |
| 8,207,392 B2 | 6/2012 | Haggstrom et al. |
| 8,235,955 B2 | 8/2012 | Blott et al. |
| 8,241,261 B2 | 8/2012 | Randolph et al. |
| 8,246,590 B2 * | 8/2012 | Hu ..................... A61F 13/02 604/119 |
| 8,273,105 B2 | 9/2012 | Cohen et al. |
| 8,353,931 B2 | 1/2013 | Stopek et al. |
| 8,376,972 B2 | 2/2013 | Fleischmann |
| 8,399,730 B2 | 3/2013 | Kazala, Jr. et al. |
| 8,409,159 B2 | 4/2013 | Hu et al. |
| 8,454,990 B2 | 6/2013 | Canada et al. |
| 8,500,704 B2 | 8/2013 | Boehringer et al. |
| 8,632,523 B2 * | 1/2014 | Eriksson ................... 604/317 |
| 8,673,992 B2 | 3/2014 | Eckstein et al. |
| 8,679,080 B2 | 3/2014 | Kazala, Jr. et al. |
| 8,680,360 B2 | 3/2014 | Greener et al. |
| 8,746,662 B2 | 6/2014 | Poppe |
| 8,764,732 B2 | 7/2014 | Hartwell |
| 8,821,535 B2 | 9/2014 | Greener |
| 8,945,030 B2 | 2/2015 | Weston |
| 9,204,999 B2 | 12/2015 | Barta et al. |
| 9,408,755 B2 | 8/2016 | Larsson et al. |
| 9,421,132 B2 | 8/2016 | Dunn |
| 2001/0029956 A1 * | 10/2001 | Argenta ................ A61M 1/005 128/897 |
| 2001/0034499 A1 | 10/2001 | Sessions et al. |
| 2002/0077661 A1 | 6/2002 | Saadat |
| 2002/0161346 A1 | 10/2002 | Lockwood et al. |
| 2004/0064132 A1 * | 4/2004 | Boehringer ............ A61F 13/02 604/543 |
| 2004/0162512 A1 | 8/2004 | Liedtke et al. |
| 2004/0267312 A1 | 12/2004 | Kanner et al. |
| 2005/0182445 A1 | 8/2005 | Zamierowski |
| 2005/0209574 A1 * | 9/2005 | Boehringer ............ A61F 13/36 604/289 |
| 2005/0267424 A1 * | 12/2005 | Eriksson ........... A61F 13/00068 604/304 |
| 2006/0020269 A1 | 1/2006 | Cheng |
| 2006/0058842 A1 | 3/2006 | Wilke et al. |
| 2006/0069357 A1 | 3/2006 | Marasco |
| 2006/0213527 A1 | 9/2006 | Argenta et al. |
| 2007/0052144 A1 | 3/2007 | Knirck et al. |
| 2007/0118096 A1 | 5/2007 | Smith et al. |
| 2007/0123973 A1 | 5/2007 | Roth et al. |
| 2007/0149910 A1 * | 6/2007 | Zocher .................. A61F 15/008 602/42 |
| 2007/0185463 A1 | 8/2007 | Mulligan |
| 2007/0213597 A1 | 9/2007 | Wooster |
| 2007/0282309 A1 | 12/2007 | Bengtson et al. |
| 2008/0041401 A1 | 2/2008 | Casola et al. |
| 2008/0071216 A1 | 3/2008 | Locke et al. |
| 2008/0095979 A1 | 4/2008 | Hatanaka et al. |
| 2008/0108977 A1 * | 5/2008 | Heaton ................ A61M 1/0011 604/543 |
| 2008/0275409 A1 | 11/2008 | Kane et al. |
| 2009/0005716 A1 | 1/2009 | Abuzaina et al. |
| 2009/0005744 A1 | 1/2009 | Karpowicz et al. |
| 2009/0076467 A1 | 3/2009 | Pinto |
| 2009/0099519 A1 | 4/2009 | Kaplan |
| 2009/0105670 A1 | 4/2009 | Bentley et al. |
| 2009/0137973 A1 | 5/2009 | Karpowicz et al. |
| 2009/0299255 A1 | 12/2009 | Kazala, Jr. et al. |
| 2010/0022990 A1 | 1/2010 | Karpowicz et al. |
| 2010/0081983 A1 | 4/2010 | Zocher et al. |
| 2010/0106188 A1 | 4/2010 | Heaton et al. |
| 2010/0121286 A1 | 5/2010 | Locke et al. |
| 2010/0121287 A1 | 5/2010 | Smith et al. |
| 2010/0125233 A1 | 5/2010 | Edward et al. |
| 2010/0160874 A1 | 6/2010 | Robinson et al. |
| 2010/0179515 A1 | 7/2010 | Swain et al. |
| 2010/0198128 A1 | 8/2010 | Turnlund et al. |
| 2010/0280468 A1 | 11/2010 | Haggstrom et al. |
| 2011/0021965 A1 | 1/2011 | Karp et al. |
| 2011/0022082 A1 | 1/2011 | Burke et al. |
| 2011/0077605 A1 | 3/2011 | Karpowicz et al. |
| 2011/0082480 A1 | 4/2011 | Viola |
| 2011/0092927 A1 | 4/2011 | Wilkes et al. |
| 2011/0110996 A1 | 5/2011 | Schoenberger et al. |
| 2011/0112458 A1 | 5/2011 | Holm et al. |
| 2011/0282310 A1 | 11/2011 | Boehringer et al. |
| 2012/0004631 A9 | 1/2012 | Hartwell |
| 2012/0016321 A1 | 1/2012 | Wu et al. |
| 2012/0029455 A1 | 2/2012 | Perez-Foullerat et al. |
| 2012/0041402 A1 | 2/2012 | Greener |
| 2012/0059412 A1 | 3/2012 | Fleischmann |
| 2012/0130326 A1 | 5/2012 | Cavanaugh, II et al. |
| 2012/0130327 A1 | 5/2012 | Marquez Canada |
| 2012/0150133 A1 | 6/2012 | Heaton et al. |
| 2012/0191054 A1 | 7/2012 | Kazala, Jr. et al. |
| 2012/0191132 A1 | 7/2012 | Sargeant |
| 2013/0131564 A1 | 5/2013 | Locke et al. |
| 2014/0094730 A1 | 4/2014 | Greener |
| 2014/0163415 A1 | 6/2014 | Zaiken et al. |
| 2014/0194836 A1 | 7/2014 | Kazala et al. |
| 2014/0207092 A1 | 7/2014 | Cavanaugh, II et al. |
| 2015/0119837 A1 | 4/2015 | Thompson, Jr. et al. |

(56) References Cited

U.S. PATENT DOCUMENTS

| 2015/0157758 | A1 | 6/2015 | Blucher et al. |
| 2015/0374561 | A1 | 12/2015 | Hubbard, Jr. et al. |
| 2016/0166254 | A1 | 6/2016 | Seegert |

FOREIGN PATENT DOCUMENTS

| CN | 101123930 | 2/2008 |
| CN | 101588836 | 11/2009 |
| CN | 102046117 | 5/2011 |
| CN | 102196830 | 9/2011 |
| CN | 102256637 | 11/2011 |
| CN | 102781380 | 11/2012 |
| DE | 2 949 920 | 3/1981 |
| DE | 10 2005 007016 | 8/2006 |
| EP | 1 320 342 | 6/2003 |
| EP | 2 279 016 | 2/2011 |
| EP | 2 298 364 | 3/2011 |
| EP | 2 529 767 | 12/2012 |
| EP | 2 567 717 | 3/2013 |
| GB | 1224009 | 3/1971 |
| GB | 2389794 | 12/2003 |
| GB | 2423019 | 8/2006 |
| GB | 2489947 | 10/2012 |
| JP | H09-503923 | 4/1997 |
| JP | 2007-505678 | 3/2007 |
| JP | 2008-529618 | 8/2008 |
| JP | 2009-536851 | 10/2009 |
| JP | 2011-500170 | 1/2011 |
| JP | 2011-523575 | 8/2011 |
| WO | WO 2001/89392 | 11/2001 |
| WO | WO 02/05737 | 1/2002 |
| WO | WO 03/003948 | 1/2003 |
| WO | WO 03/045259 | 6/2003 |
| WO | WO 2004/018020 | 3/2004 |
| WO | WO 2004/037334 | 5/2004 |
| WO | WO 2006/046060 | 5/2006 |
| WO | WO 2006/052839 | 5/2006 |
| WO | WO 2007/133618 | 11/2007 |
| WO | WO 2008/064502 | 6/2008 |
| WO | WO 2008/104609 | 9/2008 |
| WO | WO 2009/146441 | 3/2009 |
| WO | WO 2009/112062 | 9/2009 |
| WO | WO 2009/114624 | 9/2009 |
| WO | WO 2009/158132 | 12/2009 |
| WO | WO 2010/051072 | 5/2010 |
| WO | WO 2010/097570 | 9/2010 |
| WO | WO 2010/118316 | 10/2010 |
| WO | WO 2012/021553 | 2/2012 |
| WO | WO 2012/082716 | 6/2012 |
| WO | WO 2012/112204 | 8/2012 |
| WO | WO 2012/136707 | 10/2012 |
| WO | WO 2016/176513 | 11/2016 |

OTHER PUBLICATIONS

Info V.A.C. User Manual—KCI—Dec. 2006 (76 pages).
International Preliminary Report on Patentability, re PCT Application No. PCT/GB2009/000696, dated Sep. 14, 2010.
Kapischke, et al., "Self-fixating mesh for the Lichtenstein procedure-a prestudy", Langenbecks Arch Surg (2010), 395 pp. 317-322.
Written Opinion of the International Searching Authority, re PCT Application No. PCT/GB2009/000696, dated Sep. 13, 2010.
International Search Report, re PCT Application No. PCT/GB2009/000696, dated Aug. 28, 2009.
Definition of "Adhere", The Free Dictionary, accessed Mar. 23, 2017, in 6 pages. URL: http://www.thefreedictionary.com/adhere.

* cited by examiner

| Device Geometry | Surface area | θ | Force generated perpendicular to surface of attachment | Force generated parallel to surface of attachment |
|---|---|---|---|---|
| A | y | 0 | py | 0 |
| B | 1.12y | 26.57° | py | 0.5py |
| C | 1.41y | 45.00° | py | 1.0py |
| D | 3.16y | 71.57° | py | 3.0py |

VACUUM CLOSURE DEVICE

CROSS REFERENCE TO RELATED APPLICATIONS

This application is a continuation of U.S. patent application Ser. No. 12/922,118, filed Nov. 17, 2010, entitled "VACUUM CLOSURE DEVICE," which is a National Phase Application of PCT Patent Application PCT/GB2009/000696, filed Mar. 13, 2009, entitled "VACUUM CLOSURE DEVICE," which claims priority to Great Britain Application No. 0804654.2, filed Mar. 13, 2008. The contents of the aforementioned applications are hereby incorporated by reference in their entireties as if fully set forth herein. The benefit of priority to the foregoing applications is claimed under the appropriate legal basis, including, without limitation, under 35 U.S.C. §119(e).

BACKGROUND OF THE INVENTION

Field of the Invention

This invention relates to the design of tissue covering elements for use in vacuum assisted tissue apposition systems, wherein the geometry of the covering elements favours the application of contractile forces over compressive or extensive forces at the tissue interface.

Description of the Related Art

Topical negative pressure (TNP) therapy has rapidly grown to be of excellent utility in the medical field, particularly in the treatment of wounds.

A number of the current negative pressure systems available involve the application of a porous, deformable wound filler to the wound. The basic principle of TNP therapy is to create a closed cavity over the wound itself by means of a thin, flexible sealing film adhered to the patient's sound skin surrounding the wound; admitting one end of an aspirant conduit into the closed cavity, the conduit being sealed to the flexible film, for example; and connecting a distal end of the aspirant conduit to a vacuum source such as an electrically driven vacuum pump, for example, to create a pressure lower than the surrounding ambient atmospheric pressure within the wound cavity. As is known to the skilled person the lower pressure creates many beneficial therapeutic effects on the wound including increased blood flow to the wound and faster granulation of tissue, for example. When the vacuum pump is switched on, the adjacent surfaces formed cavity expand into the wound filler, compressing it up to the point where it can mechanically resist further deformation. In this state, it is hypothesised that, in a wound cavity, both compressive and extensive forces are exerted on the micro scale at the tissue surface while extensive forces are exerted on the macro scale a short distance from the tissue-filler interface. The extent of these compressive and extensive forces is determined by the applied (negative) pressure, the mechanical properties of the surrounding tissue, filler and drape and the geometry of the wound.

Figure 1:
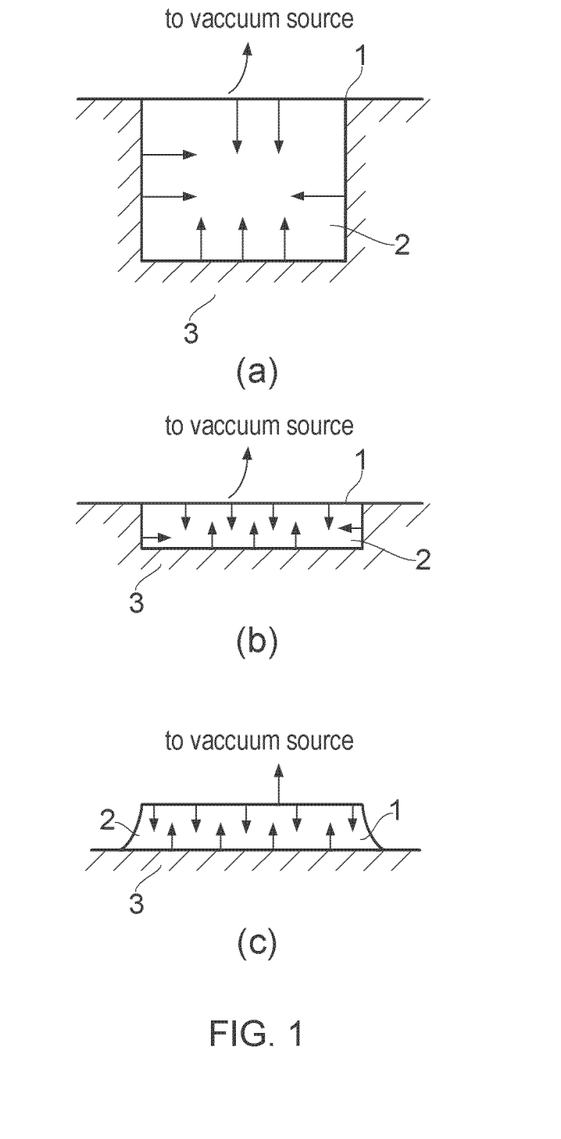
FIG. 1: Force vectors generated within hypothetical tissue cavities.
  (a) Force vectors generated by a conventional tissue covering element when applied to (a) a cavity wound (b,c) and to a largely flat or convex wound.

One TNP system provide the user with sheets of foam of varying geometry that are routinely cut to shape at the site of application to conform to the surface of the wound or fill the wound cavity. In this regard, for some applications, including those targeted here, this technique is sub-optimal. The problem here is that even if we assume uniform foam, drape and tissue mechanics across the patient population, the wound geometry will vary significantly from patient to patient. FIG. 1 demonstrates the effect of applying standard pressure and mechanics (tissue, drape and foam) to varying geometries of application; the force vectors generated vary widely. For most applications, particularly to cavity wounds, the extent of this variation is not great and does not affect the efficacy of the treatment significantly: surrounding tissue is generally expanded in the desired direction, towards the centre line of the cavity volume (see FIG. 1). However, for shallow wounds or incisional wounds, the desired mechanical forces are not afforded by the current method; in general, a compressive force perpendicular to the tissue surface is generated with a minor force generated in the direction parallel to the wound surface. For shallow wounds and incision wounds, it is desirable to generate significant forces parallel to the wound surface in the direction of wound closure in the same way as it is desirable to generate this arrangement in wound cavities by the traditional method.

We are not aware of topical negative pressure devices capable of generating significant forces parallel to largely two-dimensional surfaces of attachment.

SUMMARY OF THE INVENTION

The invention is concerned with the component of a topical or internal negative therapy apparatus which forms the interface with the tissue surface and provides a vacuum cavity above the tissue surface. Traditionally, in the field of topical negative pressure, this interface is achieved using a porous wound filler and an occlusive or semi-occlusive adhesive drape (to create the substantially air tight seal), as described above.

This device is referred to herein as the tissue covering element.

The invention is not restricted to the means of generating negative pressure or regulating negative pressure or to the means of transmitting the source of negative pressure to the site of application, but is directed to the design geometry of the tissue covering element.

The comparable component of the present invention in conventional negative pressure systems generates very low contractile forces in the plane which is parallel to largely flat or convex tissue surfaces but, in contrast, generates relatively large compressive or extensive forces in the plane which is perpendicular to the tissue surface. This is because the majority of the surface area of the vacuum cavity arranged in these cases is parallel to the tissue surface and the forces are generated perpendicular to this.

The force vectors generated are predominantly compressive forces. Such forces are appropriate for the closure of cavity wounds but are contrary to the desire for contraction of the wound margin in the direction of closure for largely flat or convex defects. As FIG. 1 band 1c further illustrate, the generation of significant forces parallel to the tissue surface cannot be achieved easily when the wound covering element is largely parallel to the tissue surface.

The present invention concerns a tissue covering element that forms an interface with largely flat or convex tissue surface geometries to generate a vacuum cavity having a geometry that is predominantly non-parallel to the tissue surface and as a consequence generates significant forces parallel to the tissue surface when the cavity is placed under reduced pressure. Preferably, the forces generated are in the direction of wound closure. It is recognised here that the 'direction of wound closure' should not only consider the geometry of the wound surface but also the mechanical properties of the surrounding tissue (e.g. Langer's lines) that may influence the most desirable geometry of closure forces.

It should be further noted that the geometry does not exclude the generation of compressive or extensive forces in the plane perpendicular to the tissue surface.

Thus, according to a first aspect of the invention there is provided a tissue covering element for use in a vacuum assisted closure system, the tissue covering element comprising:
  i) a wound contacting surface, said surface being positionable on either side of a wound margin;
  ii) a bridging portion which bridges the wound and in use provides at least a partial vacuum above the wound, and wherein the bridging portion comprises a higher ratio of internal surfaces that are aligned substantially non-parallel relative to the wounded tissue surface, to: surfaces that are aligned substantially parallel relative to the wounded contacting surface.

According to a second aspect of the invention there is provided a method of closing a wound, said method comprising;
  i) locating a tissue covering element according to the invention at a wound site such that the bridging element bridges the wound margins;
  ii) providing a device for generating a negative pressure;
  iii) applying a negative pressure to the tissue covering element in a manner such that the bridging portion of the tissue covering element creates at least a partial vacuum cavity above the wound.

A method of applying a contractile force to a wound, said method comprising;
  i) locating a tissue covering element according the invention at a wound site, such that the bridging element bridges the wound margins;
  ii) providing a device for generating a negative pressure;
  iii) applying a negative pressure to the tissue covering element in a manner such that the bridging portion of the tissue covering element creates at least a partial vacuum cavity above the wound.

According to a further aspect of the invention there is provided the use of a device according to the present invention in a vacuum assisted closure apparatus.

According to a further aspect of the invention there is provided the use of a device according to the present invention in wound therapy.

According to a further aspect of the invention there is provided the device or use of the device according to the present invention as herein described with reference to the accompanying Examples and Figures.

The contractile forces so generated, parallel to the tissue surface are transmitted to the tissue margin and this tissue experiences a force directed approximately towards the centre of the vacuum cavity.

The tissue surfaces can be largely flat or convex.

Figure 2:
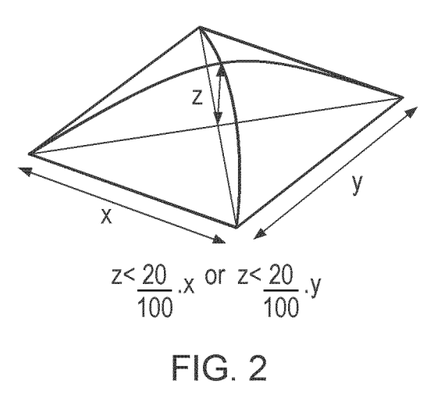
FIG. 2: Illustrates a substantially flat wound.

The term 'largely flat' is herein taken to mean surfaces with vertical dimensions no greater than 20% of the shortest of the other dimensions (FIG. 2).

The tissue surfaces can be internal or external to the body.

The tissue surfaces can be on soft tissues (e.g. skin, cartilage, tendon, ligament, muscle, fascia) or hard tissues (e.g. bone)

In embodiments of the invention such a surface geometry can be afforded by the use of corrugated or concertina-folded structures. The corrugation of the vacuum cavity cannot easily or painlessly be achieved in the tissue surface but can easily be achieved in the tissue covering element by providing corrugations that extend in the direction largely perpendicular to the tissue surface. It is important that this geometry is not completely destroyed under the influence of reduced pressure within the vacuum cavity, although some geometrical distortion is unavoidable.

It is important that the covering element is sufficiently flexible to allow good conformability across the tissue but also sufficiently rigid to maintain a higher ratio of surfaces perpendicular to the tissue surface than those parallel to the tissue surface. This combination of flexibility and rigidity can be achieved most simply by combining relatively inflexible surfaces largely perpendicular to the tissue surface with flexible hinges.

The tissue covering element of the present invention is defined as having at least 50% of its internal surface area distribution at an angle of 45° or greater relative to the underlying, largely flat or convex tissue surface. The net force is contractile.

In further specific embodiments of the invention the tissue covering element is defined as having at least 50% of its internal surface area distribution at an angle of 800 or greater relative to the underlying, largely flat or convex tissue surface. The net force is contractile.

There may be some medical applications in which it may be desired to provide a wound covering element that expands rather than contracts the wound. In such instances the tissue covering element defined as having the majority of its internal surface area distribution at an angle of between about 50 to 450 relative to the underlying, largely flat or convex tissue surface.

Figure 5:
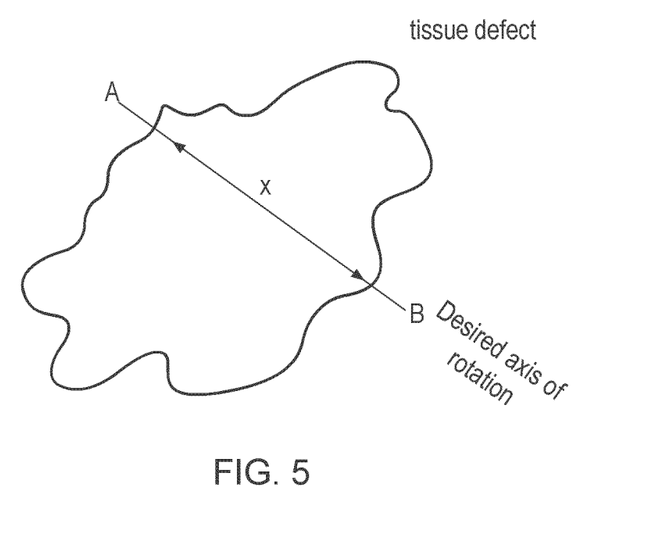
FIG. 5: Determining the optimal dimension of the tissue covering element.

The shortest distance between the margins of the wound is defined as X, and the length of the bridging element is defined as Y. In embodiments of the invention Y is at least 110% of X. In further embodiments of the invention Y is at least 141% of X, as illustrated in FIG. 5. The tissue covering element can be defined in any single dimension as one with an internal surface length not exceeding 1000% of the shortest line between opposing points on the tissue margin (FIG. 5). The additional surface length is used to generate corrugations or folds that increase the surface area of the covering non-parallel to the tissue surface with the aim of maximising the perpendicularity of the covering to the tissue surface.

For application to largely one-dimensional incision wounds, an inverted 'V' structure, as illustrated in FIG. 3c, is an advantageous geometry.

Figure 7:
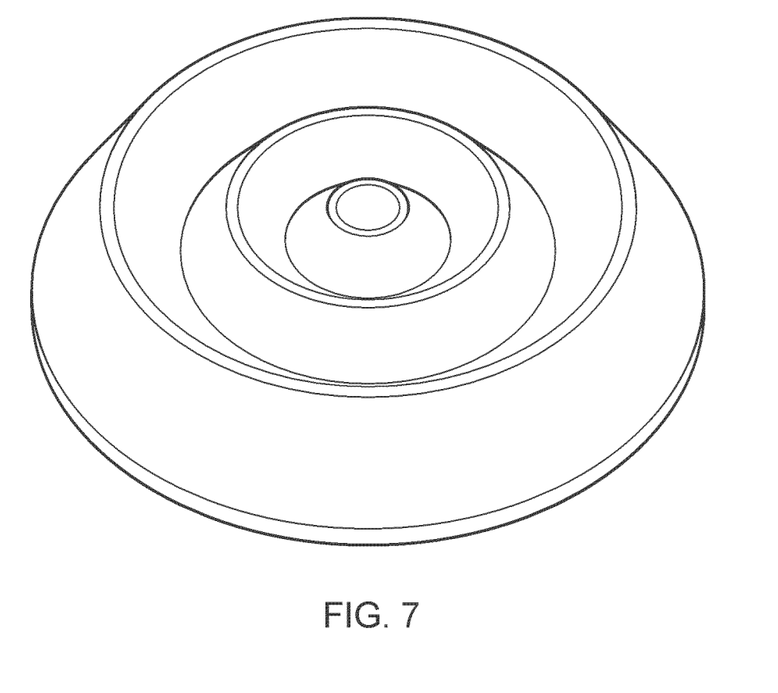
FIG. 7: A schematic of tissue covering element for application to largely flat circular wounds in locations of isotropic skin tension.

For application to largely flat circular wounds in locations of isotropic skin tension, a corrugated concentric ring structure, as illustrated in FIG. 7, is an advantageous geometry.

Figure 8:
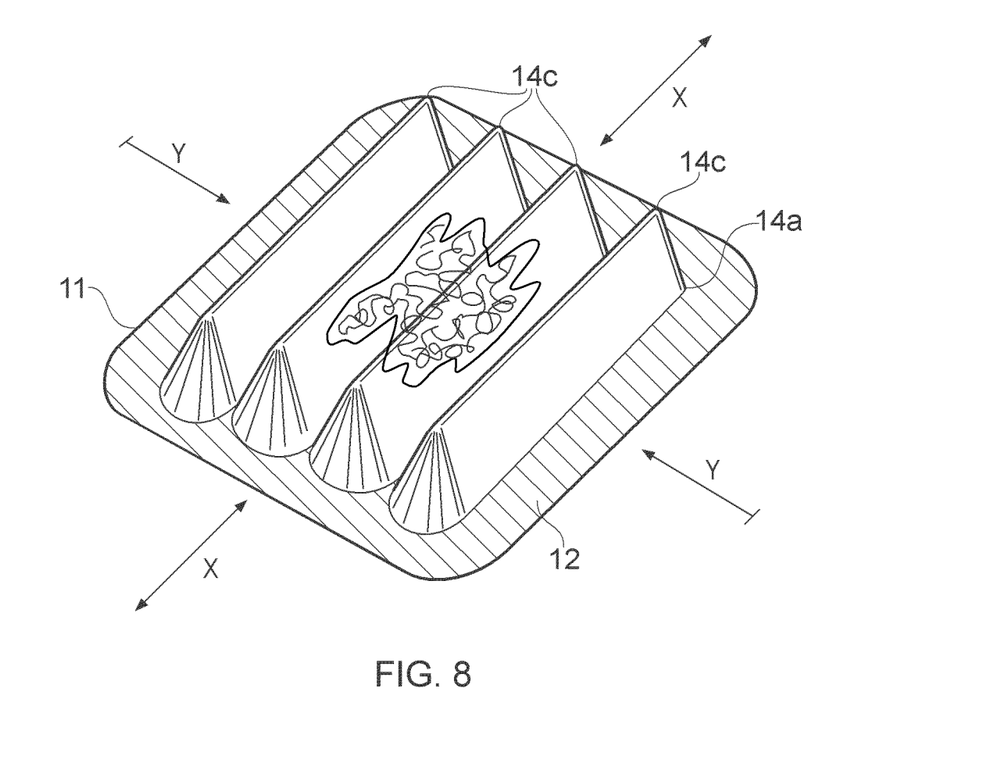
FIG. 8: A schematic of tissue covering element for application to largely flat wounds in locations of anisotropic skin tension.

For application to large flat wounds in locations of anisotropic skin tension, a multiple inverted 'V' 'concertina configuration in desirable. The lines of the concertina folds being positioned parallel to local Langer's lines to effect wound closure (FIG. 8).

For example, for application to convex surfaces, such as the extremities of the body or the bones of the body, a cylindrical concertina configuration is desirable (similar to a shock absorber 'boot'). The lines of the concertina folds being perpendicular to the axis of the limb (FIG. 9) for application to bone, or parallel to local Langer's lines to effect topical wound closure (FIG. 8).

In practical use, to avoid the eventuality where the application of negative pressure to the cavity causes gross distortion of the desired geometry of the covering, the two-dimensional surfaces of the device are constructed of relatively stiff materials in comparison to the folded regions, which should flex easily. That is not to imply the use of rigid materials, uncomfortable for the wearer.

The tissue covering element must be attached to the patient in a manner that creates an substantially air tight seal of a quality that allows the vacuum source to maintain the target vacuum level within the enclosed volume. Practically, attachment to the patient can be achieved by means of any bonding mechanism. Preferably attachment is achieved by using an adhesive, such as an acrylate- or silicone-based adhesive commonly used for the attachment of medical devices and well known in the art. It is also possible that attachment can be achieved by utilising the pressure differential alone, in the same manner as a suction cup. However, this is difficult to achieve in reality due to the mechanical properties of tissue. Connection of the enclosed volume to the vacuum source can be achieved by any means obvious to a person skilled in the art, for example via a central penetrating port or in between the covering element and the bonded perimeter. Preferably, the vacuum source is connected to the enclosed volume by a port penetrating the surface of the covering element. It is additionally beneficial for the coupling of the vacuum source to the covering element to be achieved by a reversible means to facilitate repeated connection and disconnection over the duration of dressing wear. It is also preferable that connection and disconnection can be easily achieved by the patient and applier.

The invention is not restricted to filling elements that may optionally be positioned within the vacuum enclosure.

The devices so described can be applied in a range of medical applications where generation of forces parallel to a surface of attachment is desirable for example, the joining of tissue and bone lesions or defects. Both topical and internal applications can be foreseen, from the application of contractive force to bone breaks to the closure of surface wounds, including surgical incisions.

BRIEF DESCRIPTION OF THE DRAWINGS

The invention will now be described, for illustrative purposes only, with reference to the accompanying Examples and Figures, wherein the Figures illustrate.

DETAILED DESCRIPTION OF THE PREFERRED EMBODIMENT

FIG. 1 illustrates the forces generated by conventional tissue covering elements when applied to (a) cavity tissue defect and (b,c) substantially flat or convex tissue defects.

(a) the tissue covering element 1 is applied to wound 2 within tissue 3. This is a cavity tissue defect. The application of a partial vacuum generates substantially equal compressive and contractile forces. This is optimal for the healing mechanism of this wound type.

(b) the tissue covering element 1 is applied to wound 2 within tissue 3. This is a shallow, largely flat tissue defect. The application of a partial vacuum generates predominantly compressive forces and minimal contractile forces. This is sub-optimal for the healing mechanism of this wound type in which there is a desire for contraction of the margin of the wound in the direction of the closure.

(c) the tissue covering element 1 is a molded cover which is applied to wound 2 within tissue 3 to form a vacuum cavity above the wound. The surfaces of the covering element are predominantly parallel to the surface of the wound. The application of a partial vacuum generates predominantly compressive forces and minimal contractile forces. This is sub-optimal for the healing mechanism of this wound type in which there is a desire for contraction of the margin of the wound in the direction of the closure.

FIG. 2 illustrates a substantially flat tissue defect. Such a wound has surfaces with vertical dimensions (z) no greater than 20% of the shortest of the other dimensions (x) and (y).

Figure 3:
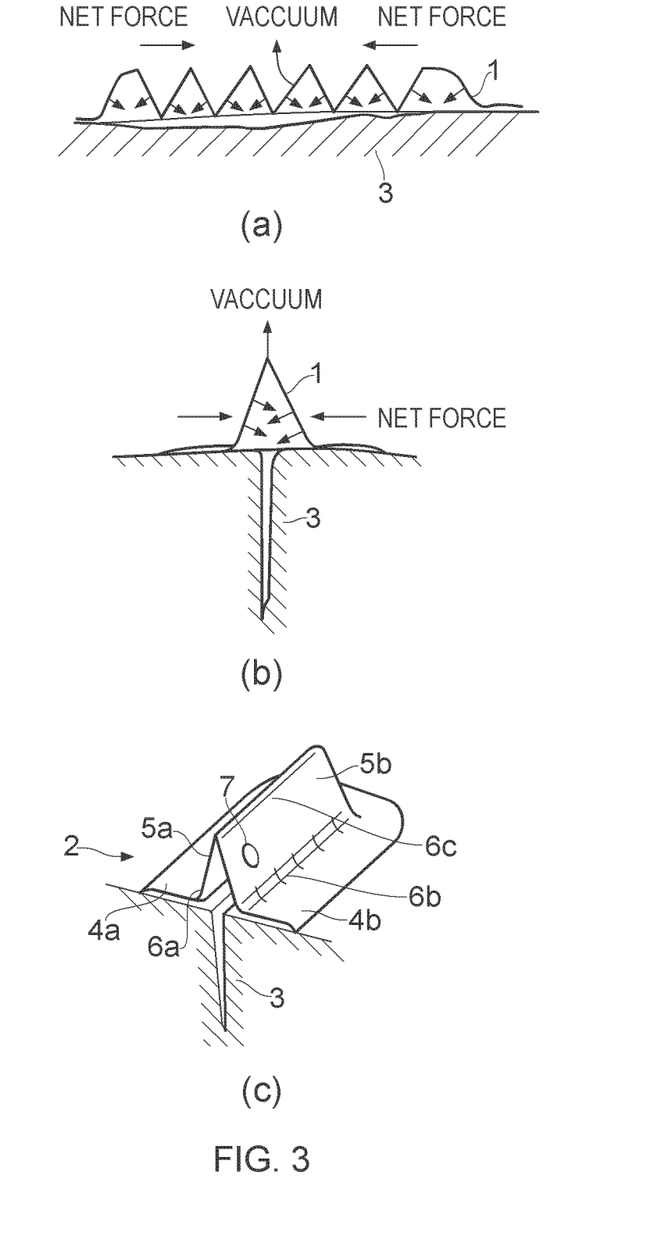
FIG. 3: Embodiments of the tissue covering element of the present invention.

FIG. 3 illustrates various embodiments of the present invention. In (a) the tissue covering element 1 which is applied to a substantially flat or convex tissue defect 3 comprises a plurality of corrugations which generate a net force parallel to the tissue surface, thereby generating a contractile force in the direction of closure of the wound. In (b) the tissue covering substantial net force is parallel to the tissue surface. In the embodiment illustrated in (c) the tissue covering element 2 comprises a base member 4a and 4b which is applied to the tissue surface 3. From this base member the walls 5a and 5b extend to the apex, thereby forming an inverted "V" shaped cavity above the surgical incision. The base member 4a and 4b and the walls 5a and 5b are made of a relatively inflexible material, with a flexible hinge 6a 6b forming the junction between the base member 4a and 4b and the walls 5a and 5b and a further flexible hinge 6c provided along the apex of the "V". A vacuum connection port 7 is provided on one of the wall elements.

Figure 4:
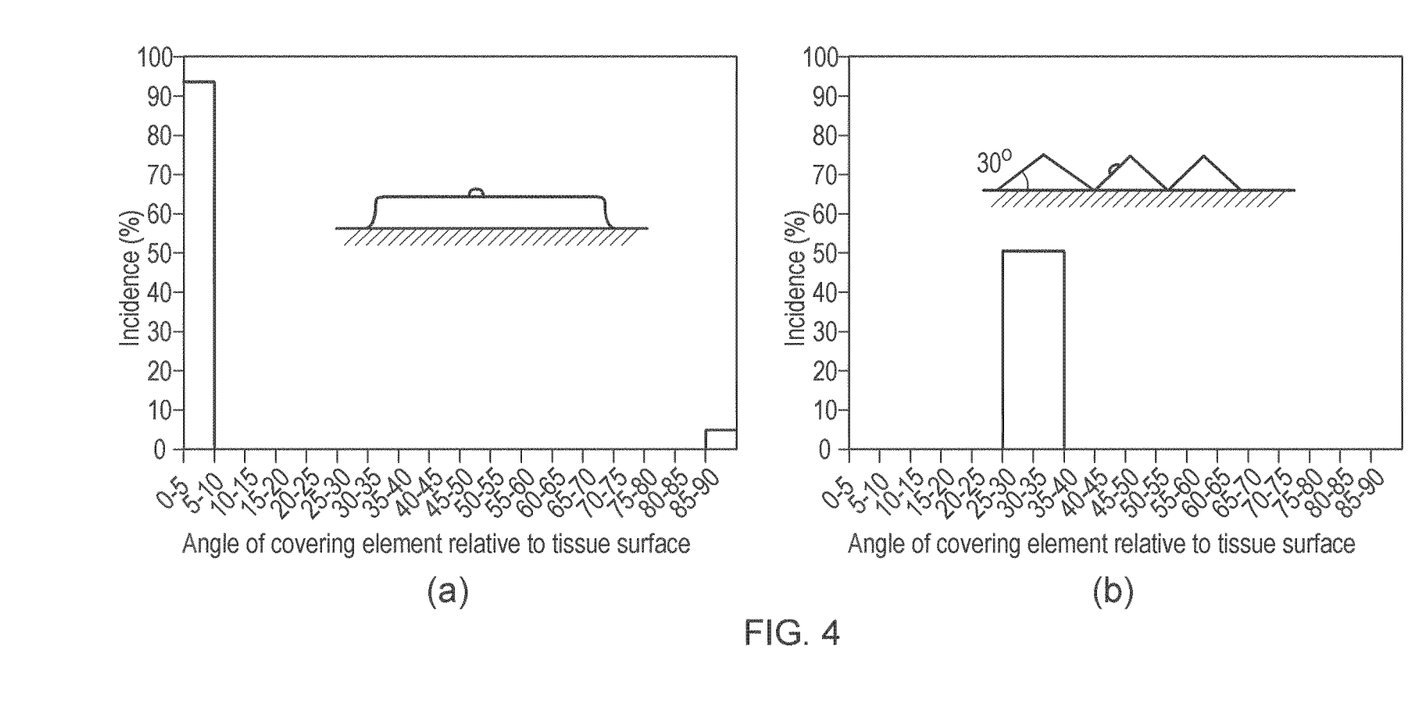
FIG. 4: The distribution of surface area angles for any given tissue covering element can be represented in a histogram.

The distribution of surface area angles for any given tissue covering element can be represented in a histogram. FIG. 4 illustrates this for the following tissue covering element designs:
  (a) a conventional negative pressure cover geometry
  (b) a cover geometry with 30° surface incidence angle
  (c) a cover geometry with 45° surface incidence angle
  (d) a hemispherical cover geometry
  (e) a cover geometry with 900 surface incidence angle
  (f) a cover geometry with 900 surface incidence angle (larger surface area than in (e)

FIG. 5 illustrates the optimal geometry of the tissue covering element relative to the tissue defect. The tissue defect has a desired axis of contraction between points A and B. The dimension of the tissue covering element aligned between A and B is preferably longer than the direct length labelled X.

Figure 6:
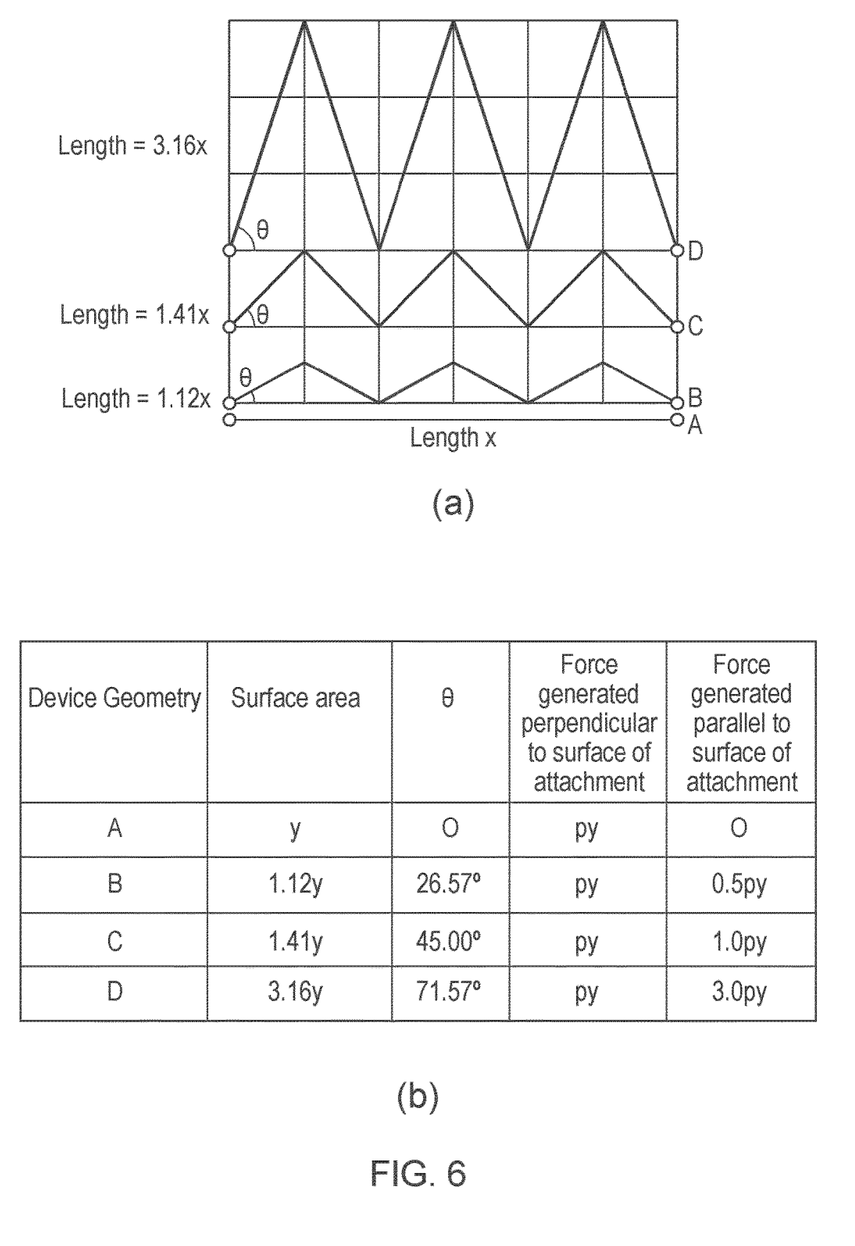
FIG. 6: Relationship between the dimension of the tissue covering element and the forces generated.

FIG. 6 illustrates that for any perimeter length the force generated perpendicular to a flat surface of attachment is constant. It can also be seen that forces generated parallel to the flat surface (contractile) scale directly in proportion to the vertical height of the corrugation divided by half its period length.

Force=Pressure×Area

Figure 9:
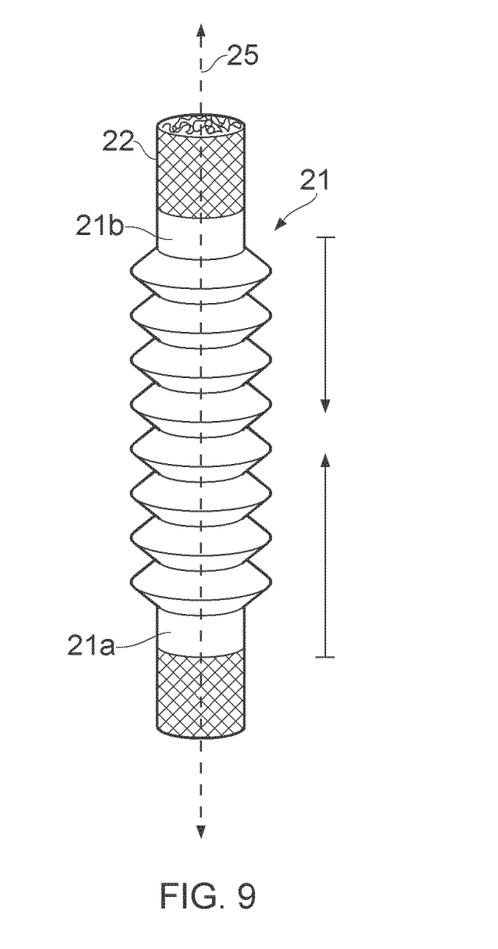
FIG. 9: A schematic of tissue covering element for application to a limb or bone tissue defect.

In the example illustrated in FIG. 6, let perimeter length x be directly proportional to surface area y (true for simple designs pictured in FIGS. 6 and 9). For a constant vacuum pressure p, the resolved forces generated from the surfaces shown in FIG. 6a are shown in FIG. 6b.

FIG. 7 is a schematic of a tissue covering element for application to largely flat circular wounds in locations of isotropic skin tension. The tissue covering element is a corrugated concentric ring structure. The centre of the element may be convex or concave when viewed from above.

FIG. 8 is a schematic of a tissue covering element for application to largely flat circular wounds in locations of anisotropic skin tension. The tissue covering element is a multiple inverted 'V' 'concertina configuration. The lines of the concertina folds being positioned parallel to local Langer's lines to effect wound closure.

The tissue covering element 11 is substantially square. An adhesive 12 forms a peripheral border around the tissue contacting surface of the tissue covering element. The element 11 further comprises a bridging element which is formed of a plurality of separated inverted V-shaped elements 13. The V-shaped elements are hinged, to allow greater flexibility. First 14a and second (not shown) hinges are provided at the join between the inverted V-shaped element and the upper surface of the tissue contacting surface (i.e. the surface that faces upwards away from the tissue). A third hinge 14c is provided at the apex of the inverted "V". The arrows "X" illustrate the direction of local Langers' lines. The arrows "Y" illustrate the direction of contraction generated under vacuum.

For application to convex surfaces, such as the extremities of the body or the bones of the body, a tissue covering element 21 having a cylindrical concertina configuration is desirable (similar to a shock absorber 'boot') as illustrated in FIG. 9. The proximal 21a and distal 21b ends of the tissue covering element are fixed to the limb or bone 22 (defect positioned under the tissue covering element). The lines of the concertina folds being perpendicular to the longitudinal axis of the limb 25. The arrow "Y" illustrates the direction of contraction generated under vacuum.

EXAMPLES

Example 1: Construction of the Incision Closure Device Pictured in FIG. 3c

A device of the design pictured in FIG. 6 was moulded using a transparent, heat-curable medical grade silicone elastomer. The device had a dome-profiled pressure cracking valve (Minivalve International B. V.) cast into one of it's cavity faces. The flat surfaces of the inverted 'V' section of the device was reinforced with pre-cured mechanically stiff silicone elastomer.

Example 2: Incision Closure with the Device of Example 1

The device prepared in Example 1 was positioned over a gaping linear incision made into a porcine belly cadaver. Partial vacuum was applied to the device via the crack-valve port. A pressure of −100 mmHg was achieved relative to ambient atmospheric pressure (660 mmHg absolute pressure). The device deformed by hinging about the highest point of the inverted 'V' section, causing contraction of the tissue around the incision in a direction perpendicular to it, thus achieving closure of the wound.

Example 3: Construction of Device for the Closure of Open Area Wounds in Langer's Line Neutral Locations A design of the concept pictured in FIG. 7 was moulded using a heatcurable medical grade silicone elastomer. The mould used was a collapsible funnel (Normann, Copenhagen) in the collapsed position. When the elastomer was cured, the concentric finned device was removed by opening the funnel.

Example 4: Radial Contraction of Tissue with the Device of Example 3

The device prepared in Example 3 was modified with a central luer lock fitting and connected to a partial vacuum of −100 mmHg relative to ambient atmospheric pressure. The device was positioned on a living person's abdomen and allowed to seal. The device corrugated under the reduced internal pressure and exerted a radial contractile force on the adjoining tissue in the direction of the centre of the device. Tissue was contracted by approximately 15% of the original device diameter.

What is claimed is:

1. A tissue stabilizing element for use in a vacuum assisted closure system, the tissue stabilizing element comprising:
   a bridging portion comprising a plurality of flat, internal surfaces, the bridging portion configured to be positioned relative to a wound;
   a vacuum connection aperture, the vacuum connection aperture disposed on the bridging portion;
   wherein the bridging portion is configured to contract to a greater extent along a first direction relative to a second direction upon application of negative pressure, the first direction parallel to the wound and the second direction perpendicular to the wound;
   wherein the flat, internal surfaces comprise faces, the faces configured to collapse toward one another upon application of negative pressure; and
   wherein the bridging portion is configured to apply a closing force to the wound along the first direction.

2. The tissue stabilizing element of claim 1, wherein the bridging portion is configured for placement over the wound.

3. The tissue stabilizing element of claim 1, wherein the bridging portion is chamfered.

4. The tissue stabilizing element of claim 1, wherein the bridging portion is corrugated.

5. The tissue stabilizing element of claim 1, wherein the bridging portion comprises a plurality of angles between the internal surfaces, the angles configured to decrease upon application of negative pressure.

6. The tissue stabilizing element of claim 1, wherein the bridging portion further comprises a plurality of hinges between the internal surfaces.

7. The tissue stabilizing element of claim 1, wherein the bridging portion is transparent.

* * * * *

UNITED STATES PATENT AND TRADEMARK OFFICE
CERTIFICATE OF CORRECTION

| | | |
|---|---|---|
| PATENT NO. | : 9,801,986 B2 | Page 1 of 1 |
| APPLICATION NO. | : 14/466892 | |
| DATED | : October 31, 2017 | |
| INVENTOR(S) | : Bryan Greener | |

It is certified that error appears in the above-identified patent and that said Letters Patent is hereby corrected as shown below:

In the Specification

In Column 2 at Line 52, Change "FIG. 1 band" to --FIGS. 1b and--.

In Column 3 at Line 59, After "bone)" insert --.--.

In Column 4 at Line 18, Change "800" to --80°--.

In Column 4 at Line 26, Change "50 to 450" to --5° to 45°--.

In Column 4 at Line 48, Change "'concertina" to --concertina--.

In Column 6 at Line 41, Change "6a 6b" to --6a and 6b--.

In Column 6 at Line 53, Change "900" to --90°--.

In Column 6 at Line 54, Change "900" to --90°--.

In Column 7 at Line 16 (approx.), Change "'concertina" to --concertina--.

Signed and Sealed this
Twelfth Day of June, 2018

Andrei Iancu
*Director of the United States Patent and Trademark Office*